US012746056B2

(12) United States Patent
Govari et al.

(10) Patent No.: US 12,746,056 B2
(45) Date of Patent: Sep. 29, 2026

(54) TEMPERATURE CONTROL FOR IRE

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 262 days.

(21) Appl. No.: 16/914,597

(22) Filed: Jun. 29, 2020

(65) Prior Publication Data

US 2021/0401490 A1 Dec. 30, 2021

(51) Int. Cl.

*A61B 18/14* (2006.01)
*A61B 18/00* (2006.01)
*A61B 18/12* (2006.01)

(52) U.S. Cl.

CPC ...... *A61B 18/1492* (2013.01); *A61B 18/1206* (2013.01); *A61B 2018/00077* (2013.01);

(Continued)

(58) Field of Classification Search

CPC ............ A61B 18/1492; A61B 18/1206; A61B 2018/126; A61B 2018/00267; A61B 2018/00613; A61B 2018/124; A61B 2018/00791; A61B 2018/00714; A61B 2018/00797; A61B 2018/00815;

(Continued)

(56) References Cited

U.S. PATENT DOCUMENTS 5,391,199 A 2/1995 Ben-Haim
5,539,199 A 7/1996 Ruckh et al.

(Continued)

FOREIGN PATENT DOCUMENTS

CN 106456241 A 2/2017
CN 206992984 U 2/2018

(Continued)

OTHER PUBLICATIONS

U.S. Appl. No. 16/842,648, filed Apr. 7, 2020.

(Continued)

*Primary Examiner* — Joseph A Stoklosa
*Assistant Examiner* — Marina Delaney Templeton
(74) *Attorney, Agent, or Firm* — Dergosits & Noah LLP; Todd A. Noah

(57) ABSTRACT

A medical apparatus includes a probe, which includes an insertion tube configured for insertion into a body cavity of a patient, a distal structure connected distally to the insertion tube and including a plurality of electrodes, which are configured to contact tissue within the body, and temperature sensors fixed to the distal structure and configured to output signals indicative of a temperature of the tissue contacted by the electrodes. The apparatus further includes an electrical signal generator configured to apply between one or more pairs of the electrodes bipolar pulses having an amplitude sufficient to cause irreversible electroporation (IRE) in the tissue contacted by the spines, and a controller configured to control a timing of the bipolar pulses applied by the electrical signal generator responsively to the signals output by the temperature sensors.

30 Claims, 6 Drawing Sheets

(52) U.S. Cl.
CPC ............... *A61B 2018/00267* (2013.01); *A61B 2018/00613* (2013.01); *A61B 2018/00791* (2013.01); *A61B 2018/126* (2013.01)

(58) Field of Classification Search
CPC .......... A61B 2018/00821; A61B 2018/00577; A61B 2018/1467; A61B 2018/00702; A61B 2018/00351; A61B 2018/00077; A61B 2018/00666; A61B 2018/0678; A61B 2017/00084; A61B 2017/00088
See application file for complete search history.

(56) References Cited

U.S. PATENT DOCUMENTS

| | | | | |
|---|---|---|---|---|
| 5,926,550 | A | 7/1999 | Davis | |
| 5,954,719 | A * | 9/1999 | Chen | A61B 18/1206 606/42 |
| 6,264,653 | B1 | 7/2001 | Falwell | |
| 8,048,067 | B2 | 11/2011 | Davalos | |
| 8,221,411 | B2 | 7/2012 | Francischelli | |
| 8,456,182 | B2 | 6/2013 | Bar-Tal et al. | |
| 10,271,893 | B2 | 4/2019 | Stewart | |
| 10,342,598 | B2 | 7/2019 | Long | |
| 10,531,914 | B2 | 1/2020 | Stewart | |
| 10,772,566 | B2 | 9/2020 | Aujila | |
| 2003/0069573 | A1* | 4/2003 | Kadhiresan | A61B 18/1492 606/41 |
| 2007/0083194 | A1* | 4/2007 | Kunis | A61B 18/1492 606/41 |
| 2007/0112342 | A1 | 5/2007 | Pearson | |
| 2008/0183251 | A1* | 7/2008 | Azar | A61B 18/14 607/101 |
| 2010/0174282 | A1 | 7/2010 | Demarais | |
| 2012/0109122 | A1 | 5/2012 | Arena et al. | |
| 2012/0220999 | A1 | 8/2012 | Long | |
| 2014/0058197 | A1 | 2/2014 | Salahieh | |
| 2016/0051324 | A1 | 2/2016 | Stewart | |
| 2016/0113709 | A1* | 4/2016 | Maor | A61B 18/1492 606/41 |
| 2017/0065330 | A1 | 3/2017 | Mickelsen et al. | |
| 2017/0105793 | A1 | 4/2017 | Cao et al. | |
| 2018/0214202 | A1 | 8/2018 | Howard et al. | |
| 2018/0221078 | A1 | 8/2018 | Howard et al. | |
| 2019/0008582 | A1* | 1/2019 | Govari | A61B 18/1206 |
| 2019/0030328 | A1* | 1/2019 | Stewart | A61B 18/1492 |
| 2019/0201089 | A1 | 7/2019 | Waldstreicher et al. | |
| 2019/0232055 | A1 | 8/2019 | Deem | |
| 2019/0350649 | A1 | 11/2019 | Sutermeister et al. | |
| 2021/0137587 | A1 | 5/2021 | Olson | |
| 2021/0146126 | A1 | 5/2021 | Waldstreicher et al. | |
| 2021/0161582 | A1 | 6/2021 | Byrd et al. | |
| 2021/0307815 | A1 | 10/2021 | Govari et al. | |
| 2022/0008123 | A1 | 1/2022 | Altmann et al. | |
| 2022/0031386 | A1 | 2/2022 | Altmann et al. | |
| 2022/0117655 | A1 | 4/2022 | Govari et al. | |
| 2023/0089295 | A1 | 3/2023 | Govari et al. | |

FOREIGN PATENT DOCUMENTS

| | | | |
|---|---|---|---|
| EP | 0358336 | A1 | 3/1990 |
| EP | 3424453 | A1 | 1/2019 |
| EP | 3960105 | A1 | 3/2022 |
| JP | 2009500052 | A | 1/2009 |
| JP | 2017205518 | A | 11/2017 |
| JP | 2019500170 | A | 1/2019 |
| RU | 2592781 | C2 | 7/2016 |
| WO | 9944524 | A2 | 9/1999 |
| WO | WO2015049784 | A1 | 4/2015 |
| WO | 2017119934 | A1 | 7/2017 |
| WO | 2018005511 | A1 | 1/2018 |
| WO | 2018191149 | A1 | 10/2018 |
| WO | 2019023280 | A1 | 1/2019 |
| WO | 2019084317 | A1 | 5/2019 |
| WO | 2021127558 | A1 | 6/2021 |
| WO | 2022028337 | A1 | 2/2022 |

OTHER PUBLICATIONS

Extended European Search Report, received for European Application No. 21165811.7, mailed on Sep. 23, 2021, 11 pages.
Extended European Search Report, received for European Application No. 23211438.9, mailed on Apr. 25, 2024, 8 pages.
Unpublished U.S. Appl. No. 17/974,738, filed Oct. 27, 2022, 22 pages.
Search Report from corresponding Japanese Patent Application No. 2021056921 dated Sep. 27, 2024.

* cited by examiner

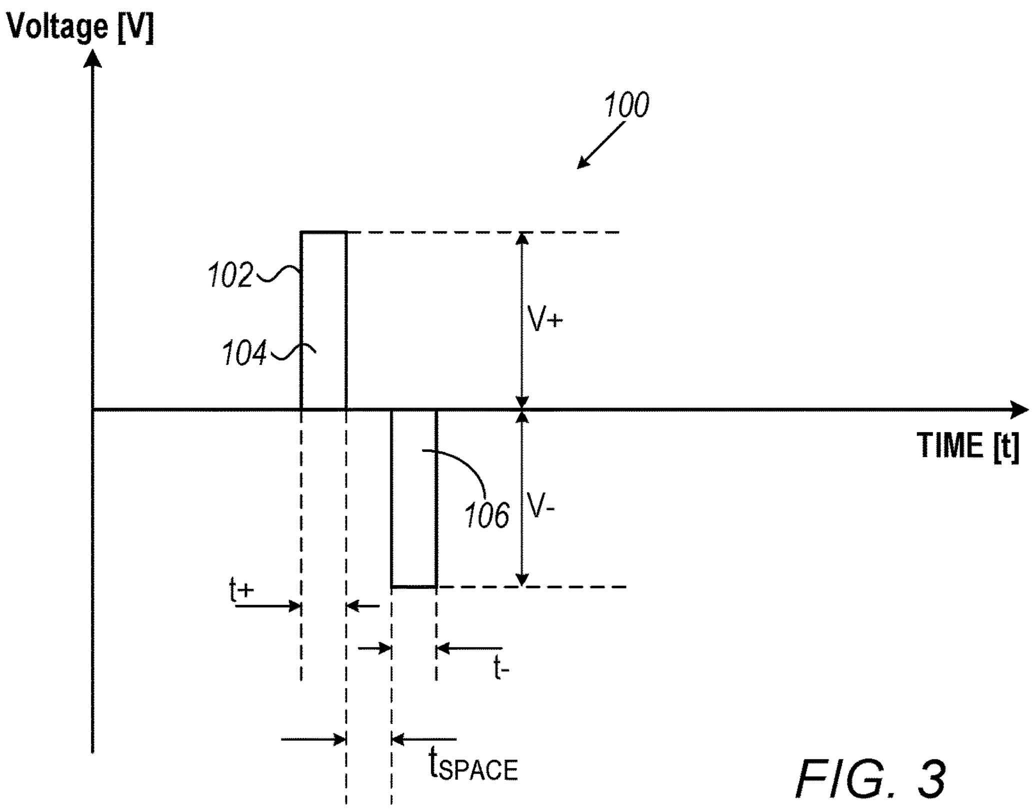
FIG. 3
FIG. 4
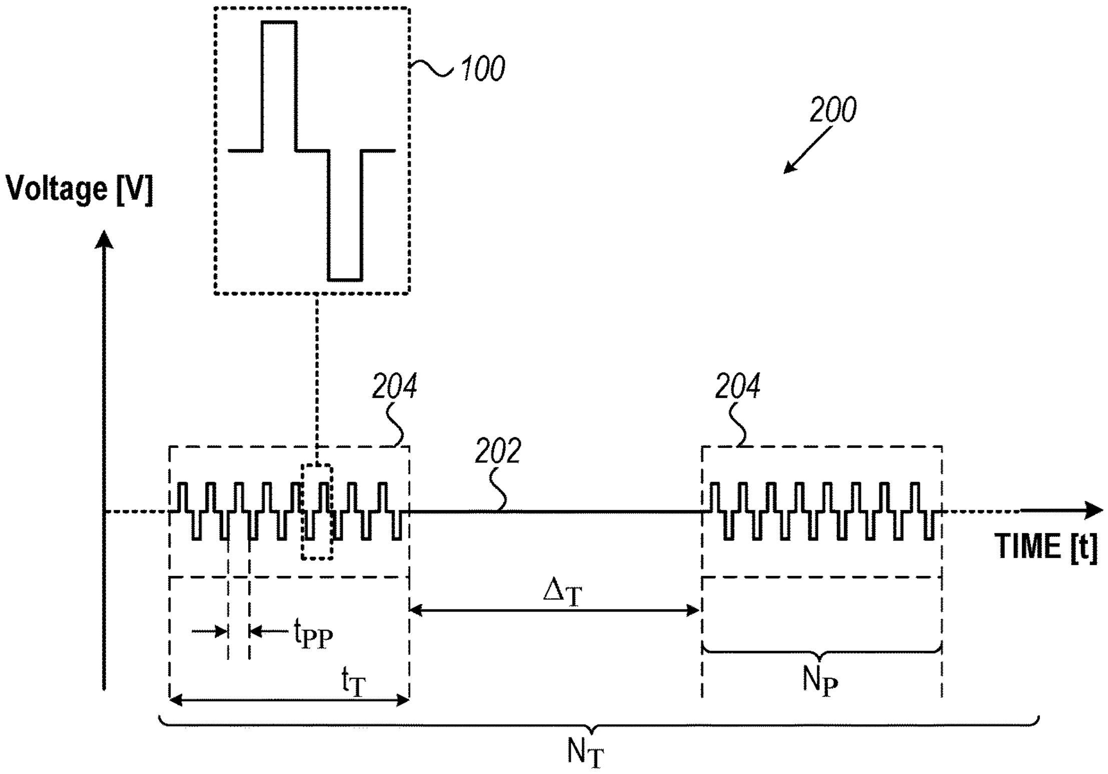

TEMPERATURE CONTROL FOR IRE

FIELD OF THE INVENTION

The present invention relates generally to medical equipment, and particularly to apparatus and methods for ablating tissue within the body.

BACKGROUND

Irreversible electroporation (IRE) is a soft tissue ablation technique that applies short pulses of strong electrical fields to create permanent and hence lethal nanopores in the cell membrane, thus disrupting the cellular homeostasis (internal physical and chemical conditions). Cell death following IRE results from apoptosis (programmed cell death) and not necrosis (cell injury, which results in the destruction of a cell through the action of its own enzymes) as in other and other radiation-based ablation techniques. IRE is commonly used in tumor ablation in regions where precision and conservation of the extracellular matrix, blood flow and nerves are of importance.

SUMMARY

Embodiments of the present invention that are described hereinbelow provide improved systems and methods for ablation of tissue in the body.

There is therefore provided, in accordance with an embodiment of the present invention, a medical apparatus, which includes a probe. The probe includes an insertion tube configured for insertion into a body cavity of a patient, and a distal structure connected distally to the insertion tube. The distal structure includes a plurality of electrodes, which are configured to contact tissue within the body, and temperature sensors fixed to the distal structure and configured to output signals indicative of a temperature of the tissue contacted by the electrodes. The medical apparatus further includes an electrical signal generator configured to apply between one or more pairs of the electrodes bipolar pulses having an amplitude sufficient to cause irreversible electroporation (IRE) in the tissue contacted by the spines, and a controller configured to control a timing of the bipolar pulses applied by the electrical signal generator responsively to the signals output by the temperature sensors.

In a disclosed embodiment, the controller is configured to modify the bipolar pulses applied by the signal generator, while the signals output by the temperature sensors indicate that the temperature of the tissue contacted by a given pair of the electrodes exceeds a preset threshold.

In a further disclosed embodiment, modifying the bipolar pulses includes preventing the electrical signal generator from applying the bipolar pulses between the given pair of the electrodes. Additionally or alternatively, the controller is configured to apply bipolar pulses to another pair of the electrodes while waiting for the temperature sensors to indicate that the temperature of the tissue contacted by the given pair of the electrodes has dropped below the preset threshold.

In some embodiments, modifying the bipolar pulses includes modifying a number of successive bipolar pulses applied by the signal generator to the given pair of the electrodes. Additionally or alternatively, modifying the bipolar pulses includes delaying application of the bipolar pulses to the given pair of the electrodes.

In a disclosed embodiment, the distal structure includes a basket assembly including a plurality of resilient spines, which are configured to contact the tissue, wherein the temperature sensors are fixed to the spines.

In a further embodiment, the spines have respective proximal and distal tips, wherein the proximal tips of the spines are joined mechanically at a proximal end of the basket assembly, and the distal tips of the spines are joined mechanically at a distal end of the basket assembly, and the spines bow radially outward when the basket assembly is deployed in the body cavity, thereby contacting the tissue in the body cavity.

In yet further embodiments, the spines include a conductive material, such as a nickel-titanium alloy, and are configured to serve as the electrodes.

In a disclosed embodiment, each spine is divided into two or more mechanically connected but electrically isolated parts, wherein the electrically isolated parts of a given spine can be electrically connected together to serve as the electrodes for applying the bipolar pulses.

In a further embodiment, the electrical signal generator is configured to apply the bipolar pulses between first and second sets of the spines, wherein at least one of the sets includes two or more of the spines.

In yet another embodiment, the insertion tube includes a flexible catheter configured for insertion into a chamber of a heart of the patient, and the electrodes are configured to contact and apply the electrical signals to myocardial tissue within the chamber.

In a disclosed embodiment the bipolar pulses applied by the electrical signal generator include a sequence of bipolar pulses having an amplitude of at least 200 V, and a duration of each of the bipolar pulses is less than 20 μs. Alternatively or additionally, the sequence of the bipolar pulses includes pairs of pulses, wherein each pair includes a positive pulse and a negative pulse.

There is additionally provided, in accordance with an embodiment of the present invention, a method for medical treatment, the method including inserting a probe including an insertion tube and a distal structure including a plurality of electrodes into a body cavity of a patient so that the electrodes contact tissue within the body cavity, applying between two or more sets of the electrodes bipolar pulses having an amplitude sufficient to cause irreversible electroporation (IRE) in the tissue contacted by the electrodes, each set including one or more of the electrodes, measuring a temperature of the tissue contacted by the electrodes and controlling a timing of the applied bipolar pulses responsively to the measured temperature.

BRIEF DESCRIPTION OF THE DRAWINGS

The present invention will be more fully understood from the following detailed description of the embodiments thereof, taken together with the drawings in which:

FIG. 3 is a schematic illustration of a bipolar IRE pulse, in accordance with an exemplary embodiment of the invention;

FIG. 4 is a schematic illustration of a burst of bipolar pulses, in accordance with an exemplary embodiment of the invention;

DETAILED DESCRIPTION OF EMBODIMENTS

Overview

IRE is a predominantly non-thermal process, which causes an increase of the tissue temperature by, at most, a few degrees for a few seconds. It thus differs from RF (radio frequency) ablation, which raises the tissue temperature by between 20° C. and 70° C. and destroys cells through heating. IRE utilizes bipolar pulses, i.e., combinations of positive and negative pulses, in order to avoid muscle contraction from a DC voltage.

For application of electroporation to a large area of tissue, a basket catheter with conductive spines may be used. A basket catheter of this sort is described, for example, in U.S. patent application Ser. No. 16/842,648, filed Apr. 7, 2020, whose disclosure is incorporated herein by reference as though set forth in its entirety. All or some of the spines contact tissue in a body cavity, such as myocardial tissue in the heart. Each spine acts as an electrode, and an electrical signal generator applies bipolar pulses between one or more pairs of the spines with an amplitude sufficient to cause IRE in the tissue contacted by the spines.

Basket catheters with this sort of conductive spines are not generally equipped with irrigation due to the complexity of such an addition. The lack of irrigation, however, may lead to overheating of tissue, as no irrigation fluid is available for carrying away the thermal energy that the IRE signals inject into the tissue.

The exemplary embodiments of the present invention that are described herein address this problem by providing temperature sensors fixed to the spines of the catheter. The temperature sensors output signals indicative of a temperature of the tissue contacted by the spines. A controller, controls the timing of the bipolar IRE pulses responsively to the signals output by the temperature sensors.

In some exemplary embodiments, the controller applies a novel control algorithm, with the objective of holding the temperature of the tissue below a certain limit. In one exemplary embodiment, this control algorithm prevents the electrical signal generator from applying bipolar pulses while the signals output by the temperature sensors indicate that the temperature of the tissue exceeds a preset threshold. While bipolar pulses are not applied to a given pair of spines due to an elevated temperature of the tissue adjacent to these spines, the control algorithm may direct bipolar pulses to be applied to another pair of spines.

In another exemplary embodiment, the control algorithm reduces the number of bipolar pulses applied in a given pulse train, until the application of this reduced pulse train is found to keep the temperature of the tissue below the preset threshold.

System Description

Figure 1:
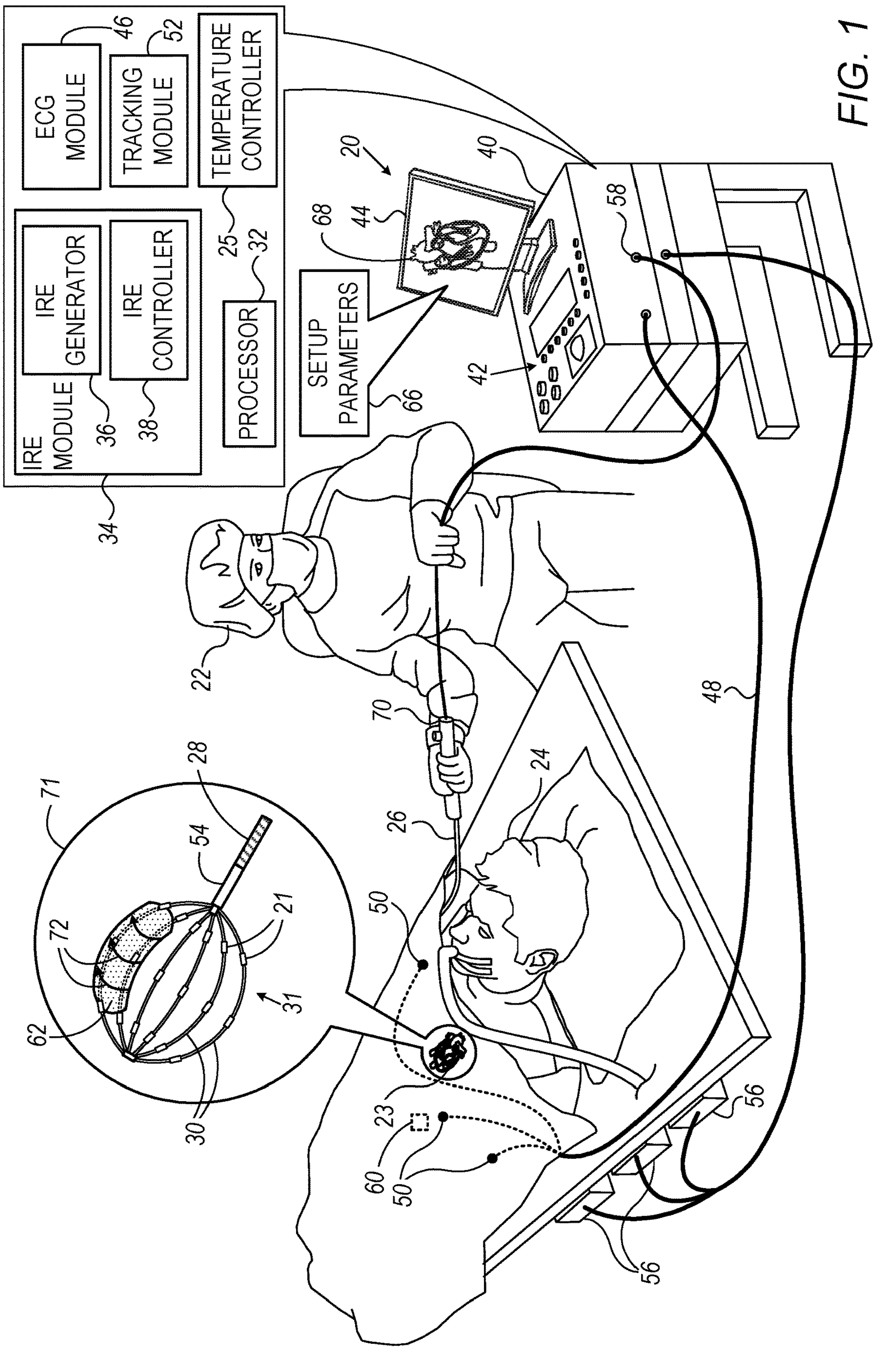
FIG. 1 is a schematic pictorial illustration of a system used in an IRE ablation procedure, in accordance with exemplary embodiments of the invention.

FIG. 1 is a schematic pictorial illustration of a system 20 used in an IRE ablation procedure, in accordance with exemplary embodiments of the present invention. In the following description, the IRE ablation procedure will also be referred to as "IRE ablation" or "IRE procedure." In the illustrated exemplary embodiment, a physician 22 is performing an IRE ablation procedure in a heart 23 of subject 24 using system 20. Physician 22 is performing the procedure using an ablation catheter 26 comprising an insertion tube 28 with/defining a longitudinal axis 27, wherein a distal end 29 of the insertion tube is connected to a basket assembly 31 comprising multiple conductive spines 30 (illustrated in greater detail in FIG. 2). For monitoring the temperature of the tissue 62 of heart 23, multiple thermal sensors 21, such as thermocouples, are attached to spines 30.

IRE system 20 comprises a processor 32, an IRE module 34, and a temperature controller 25. IRE module 34 comprises an IRE generator 36 and an IRE controller 38, wherein the IRE generator 36 comprises a dedicated pulse generator, as described further hereinbelow. IRE generator 36 generates, under the control of IRE controller 38, IRE signals, which comprise trains of bipolar electrical pulses. The pulses are directed to selected spines 30, which serve as electrodes for performing an IRE procedure, and give rise to electroporation currents 72, which flow through tissue 62. Processor 32 handles the input and output interfaces between IRE system 20 and physician 22, as well as the communication to IRE controller 38. The bipolar electrical pulses and IRE module 34 are further described below with reference to FIGS. 3-5.

During IRE ablation, currents 72 also heat tissue 62 due to Joule heating. Due to the complexity of adding irrigation to basket assembly 31, there may not be sufficient cooling of tissue 62 by naturally circulating bodily fluids, and the tissue may overheat, causing, for example, charring or bubbles in the surrounding blood. To prevent overheating, thermocouples 21 and temperature controller 25 are deployed to provide feedback to IRE controller 38. On this basis, the IRE controller 38 gates the timing and the issuance of IRE pulses by IRE module 34 so that the temperature of tissue 62 remains below a preset limit. Further details of the temperature control strategy used by temperature controller 25 are given hereinbelow.

Processor 32 typically comprises a programmable processor, which is programmed in software and/or firmware to carry out the functions that are described herein. IRE controller 38 and temperature controller 25 are likewise implemented in software and/or firmware either on the same or another programmable processor. Alternatively or additionally, these components of system 20 may comprise hard-wired and/or programmable hardware logic circuits, which carry out at least some of these functions. Temperature controller 25 additionally comprises circuitry such as analog-to-digital converters for receiving and converting the analog signals from thermocouples 21 into a digital form. IRE generator 36 comprises analog and digital components and assemblies, for generating the IRE signals that are directed to spines 30. Although processor 32, IRE generator 36, IRE controller 38, and temperature controller 25 are shown in the figures, for the sake of simplicity, as separate, monolithic functional blocks, in practice some of these functions may be combined in a single processing and control unit.

Processor 32, IRE module 34, and temperature controller 25 typically reside within a console 40. Console 40 comprises input devices 42, such as a keyboard and a mouse. A display screen 44 is located in proximity to (or integral to) console 40. Display screen 44 may optionally comprise a touch screen, thus providing another input device.

IRE system 20 may additionally comprise one or both of the following modules (typically residing within console 40), connected to suitable interfaces and devices in system 20:

An electrocardiogram (ECG) module 46 is coupled through a cable 48 to ECG electrodes 50, which are attached to subject 24. ECG module 46 is configured to measure the electrical activity of heart 23.

A tracking module 52 is coupled to one or more electromagnetic position sensors 54 in the distal end of insertion tube 28, and possibly within basket assembly 31, as well. In the presence of an external magnetic field generated by one or more magnetic-field generators 56, electromagnetic position sensors 54 output signals that vary with the positions of the sensors. Based on these signals, tracking module 52 tracks the positions of spines 30 in heart 23.

The above modules 46 and 52 typically comprise both analog and digital components, and are configured to receive analog signals and transmit digital signals. Each module may additionally comprise hard-wired and/or programmable hardware logic circuits, which carry out at least some of the functions of the module.

Catheter 26 is coupled to console 40 via an electrical interface 58, such as a port or socket. IRE signals are thus carried from IRE generator 36 via interface 58 and wiring inside insertion tube 28 to spines 30 in basket assembly 31. Temperature signals from thermocouples 21 are carried from distal end 28 via interface 58 to temperature controller 25. Similarly, signals for tracking the position and orientation of distal end 28 may be received by tracking module 52 via interface 58.

An external electrode 60, or "return patch," may be additionally coupled externally between subject 24, typically on the skin of the subject's torso, and IRE module 34. External electrode 60 may be used for coupling IRE signals between one of spines 30 and the external electrode, thus achieving electroporation that is localized deeper in tissue 62.

Processor 32 receives from physician 22 (or from another user), prior to and/or during the IRE procedure, setup parameters 66 for the procedure. Using one or more suitable input devices 42, physician 22 sets setup parameters 66, selecting one or more pairs of spines 30 to serve as electrodes for activation (for receiving the IRE signals) and the order in which the electrodes are activated, as well as defining the characteristics (timing and amplitude) of the IRE signals. Physician 22 also determines a preset limit $T_{th}$ for tissue temperature to be utilized by temperature controller 25 in the temperature control process. Alternatively, the limit may be set automatically to a default value. Additionally, processor 32 may display setup parameters 66 on display screen 44.

As used herein, the terms "one or more pairs of spines" and "electrode pairs" are not limited to one spine and an adjacent spines (or one electrode and an adjacent electrode), but rather refer to all possible configurations that allow for delivery of biphasic energy between (a) two singular spines acting as two separate electrodes or (b) between two groups of multiple spines. For case (a), one example of two singular spines acting as an electrode "pair" can be spine 30*a* in FIG. 2 as one electrode in concert with adjacent spine 30*b*, thus defining a "pair of electrodes" when biphasic voltage is delivered to this pair of spines 30*a* and 30*b*. Alternatively, spine 30*a* can be paired with a non-neighboring spine 30*c* as "another pair"; spine 30*a* with non-neighboring spine 30*d* as yet another "electrode pair"; spine 30*a* with distant spine 30*f* as a further "electrode pair"; or spine 30*b* with distant spine 30*d* as yet another "pair." In a further example of case (a), alternating spines 30*a* and 30*c* can be energized as one "electrode pair," and alternating spines 30*b* and 30*d* energized as a different "electrode pair," and so on in various permutations. For case (b) relating to a group of spines acting as one electrodes in concert with another group of different spines acting as another electrode for a "pair of electrodes," two or more spines (e.g., 30*a* and 30*b*) can act as one electrode to operate with two or more spines (30*c* and 30*d*) grouped together as another electrode, and thus to define an "electrode pair" for delivery of biphasic energy to the electrodes (i.e., spines 30*a* and 30*b* as one electrode and spines 30*c* and 30*d* as the other electrode to define an "electrode pair"). Various permutations of single spines acting as a pair of electrodes can be combined with groups of spines acting as electrode pairs and are considered to be within the scope of the present invention. For example, the spines shown in FIG. 2 can be utilized to define two electrode pairs: spines 30*a* and 30*b* define one electrode pair, while group of spines 30*c*+30*d* (one electrode) and group of spines 30*e*+30*f* (as another electrode) define the second electrode pairs.

In some exemplary embodiments, processor 32 displays on display 44, based on signals received from tracking module 60, a relevant image 68 of the subject's anatomy, such as a map of a chamber of heart 23, which is annotated, for example, to show the current position and orientation of basket assembly 31. Alternatively or additionally, based on signals received from ECG module 46, processor 32 may display on display screen 44 the electrical activity of heart 23.

To begin the procedure, physician 22 inserts catheter into subject 24, for example through the subject's vascular system, and then navigates insertion tube 28, using a control handle 70, to an appropriate site within, or external to, heart 23. At the insertion and navigation stage, basket assembly 31 is in a collapsed form, generally inside a sheath (not shown), in order to provide for an easy insertion into subject 24.

Once insertion tube 28 is positioned in the required area within heart 23, basket assembly 31 is advanced from the sheath, assuming an expanded form. A further detailed description of basket assembly 31 is given in FIG. 2, below. As shown schematically in an inset 71, physician 22 now brings basket assembly 31 into contact with tissue 62 of heart 23, such as myocardial or epicardial tissue. Next, IRE generator 36, under the control of IRE controller 38, generates IRE signals comprising trains of pulses (shown in detail in FIG. 4). The IRE signals are carried through catheter 26, over different respective electrical conductors (not shown), to pairs of spines 30, such that currents 72 generated by the IRE signals flow between the spines in each pair (bipolar ablation), and perform the desired irreversible electroporation of tissue 62 over the extended area between the spines. During the IRE procedure, temperature controller 25 continuously measures the temperature of tissue 62 via thermocouples 21, and, in conjunction with IRE controller 38, controls the timing of the IRE signals generated by IRE module 34 so as to keep the tissue temperature below the preset limit $T_{th}$.

A commonly used default value for $T_{th}$ is chosen as 5° C. above a temperature baseline of 38° C., i.e., $T_{th}$ is chosen to be 43° C. Alternatively, physician 22 may adjust the value of $T_{th}$ by choosing (generally) a lower baseline value, especially if catheter 26 is equipped with irrigation. In such a case, the preset limit $T_{th}$ may be adjusted to be in the range of 38° C.-43° C.

Further details of the temperature control strategy used by temperature controller 25 are given hereinbelow.

Figure 2:
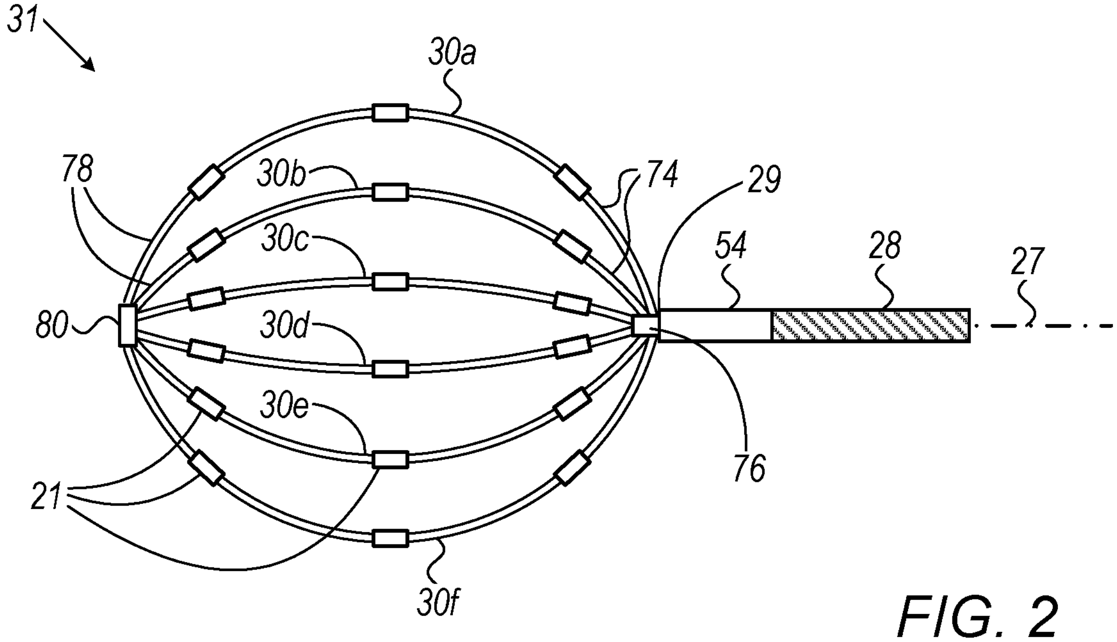
FIG. 2 is a schematic side view of a basket assembly, in accordance with an exemplary embodiment of the invention.

FIG. 2 is a schematic side view of basket assembly 31, in accordance with an exemplary embodiment of the present invention. Basket assembly 31 comprises spines 30, which are in FIG. 2 labelled individually as 30*a*, 30*b*, 30*c*, 30*d*, 30*e*, and 30*f*. (In some of the descriptions below, general indices such as 30*i* and 30*j* will be used.) Spines 30*a*-30*f* comprise long segments of a resilient material, which is conductive or has a conductive coating or a conductive member attached to it. For example, spines 30*a*-30*f* may comprise a nickel-titanium alloy, known as nitinol. Each spine 30 has one or more thermocouples 21 attached to it for measuring the local temperature of tissue 62 adjacent to the thermocouple.

Proximal tips 74 of spines 30*a*-30*f* are joined mechanically at proximal end 76 of basket assembly 31, and distal tips 78 of the spines are joined mechanically at a distal end 80 of the basket assembly. Proximal and distal tips 74 and 78, respectively, of spines 30*a*-30*f*, however, are insulated electrically from one another so that the spines can serve as separate electrodes. Spines 30*a*-30*f* are fabricated so that basket assembly 31 has an expanded state as its stable state. Thus, spines 30*a*-30*f* bow radially outward when the basket assembly is deployed in a body cavity, thereby contacting tissue 62 in the body cavity. Spines 30*a*-30*f* are electrically coupled via conductors within catheter 26 to IRE generator 36 (FIG. 1) for receiving IRE ablation signals, and thermocouples 21 are similarly electrically coupled to temperature controller 25.

The IRE signals received from IRE generator 36 are coupled, for example, between spines 30*a* and 30*b*, causing the electroporation to take place between these two spines. Due to the applied IRE signals, currents 72 (FIG. 1) flow between spines 30*a* and 30*b* along their entire length, thus causing electroporation over a large area in tissue 62. For example, applying basket assembly 31 to pulmonary vein ablation will cause electroporation over a 6-12 mm wide ring around the pulmonary vein.

The IRE signals may be coupled between any pair of spines 30*a*-30*f*, although typically the signals will be applied between pairs of adjacent spines. Additionally or alternatively, the signals may be applied simultaneously or in alternation between several pairs of spines. Although basket assembly 31 is depicted in FIG. 2 to comprise six spines, other numbers of spines, both smaller and larger than six, may be used. Additionally or alternatively, a set of multiple spines 30 may be electrically connected together to form a larger "virtual electrode" comprising multiple spines. IRE signals may be applied between one or more pairs of these "virtual electrodes" or sets.

In a further exemplary embodiment, each spine 30 may be divided into two or more sub-electrodes for measuring and mapping electrophysiological signals. In other words, each spine 30 is divided into two or more mechanically connected but electrically isolated parts. For electroporation, the sub-electrodes on each spine 30 are connected together (shorted) so that each spine functions as a single electroporation electrode.

FIG. 3 is a schematic illustration of a bipolar IRE pulse 100, in accordance with an embodiment of the invention.

A curve 102 depicts the voltage V of bipolar IRE pulse 100 as a function of time t in an IRE ablation procedure. Bipolar IRE pulse 100 comprises a positive pulse 104 and a negative pulse 106, wherein the terms "positive" and "negative" refer to an arbitrarily chosen polarity of the two spines 30 between which the bipolar pulse is applied. The amplitude of positive pulse 104 is labeled as V+, and the temporal width of the pulse is labeled as t+. Similarly, the amplitude of negative pulse 106 is labeled as V−, and the temporal width of the pulse is labeled as t−. The temporal spacing between positive pulse 104 and negative pulse 106 is labeled as $t_{SPACE}$. Typical values for the parameters of bipolar pulse 100 are given in Table 1, below.

FIG. 4 is a schematic illustration of a burst 200 of bipolar pulses, in accordance with an exemplary embodiment of the invention.

In an IRE procedure, the IRE signals are delivered to spines 30 as one or more bursts 200, depicted by a curve 202. Burst 200 comprises $N_T$ pulse trains 204, wherein each train comprises $N_P$ bipolar pulses 100. The length of pulse train 204 is labeled as $t_T$. The period of bipolar pulses 100 within a pulse train 204 is labeled as $t_{PP}$, and the interval between consecutive trains is labeled as $\Delta_T$, during which the signals are not applied. Typical values for the parameters of burst 200 are given in Table 1, below.

TABLE 1

Typical values for the parameters of IRE signals

| Parameter | Symbol | Typical values |
|---|---|---|
| Pulse amplitudes | V+, V− | 200-2000 V |
| Pulse widths | t+, t− | 0.5-5 μs |
| Spacing between positive and negative pulse | $t_{SPACE}$ | 0.1-5 μs |
| Period of bipolar pulses in a pulse train | $t_{PP}$ | 1-20 μs |
| Length of pulse train | $t_T$ | 5-100 μs |
| Number of bipolar pulses in a pulse train | $N_P$ | 1-100 |
| Spacing between consecutive pulse trains | $\Delta_T$ | 0.3-1000 ms |
| Number of pulse trains in a burst | $N_T$ | 1-100 |
| Length of a burst | | 0-500 ms |
| Energy per channel | | ≤60 J |
| Total time for IRE signal delivery | | ≤10 s |

Figure 5:
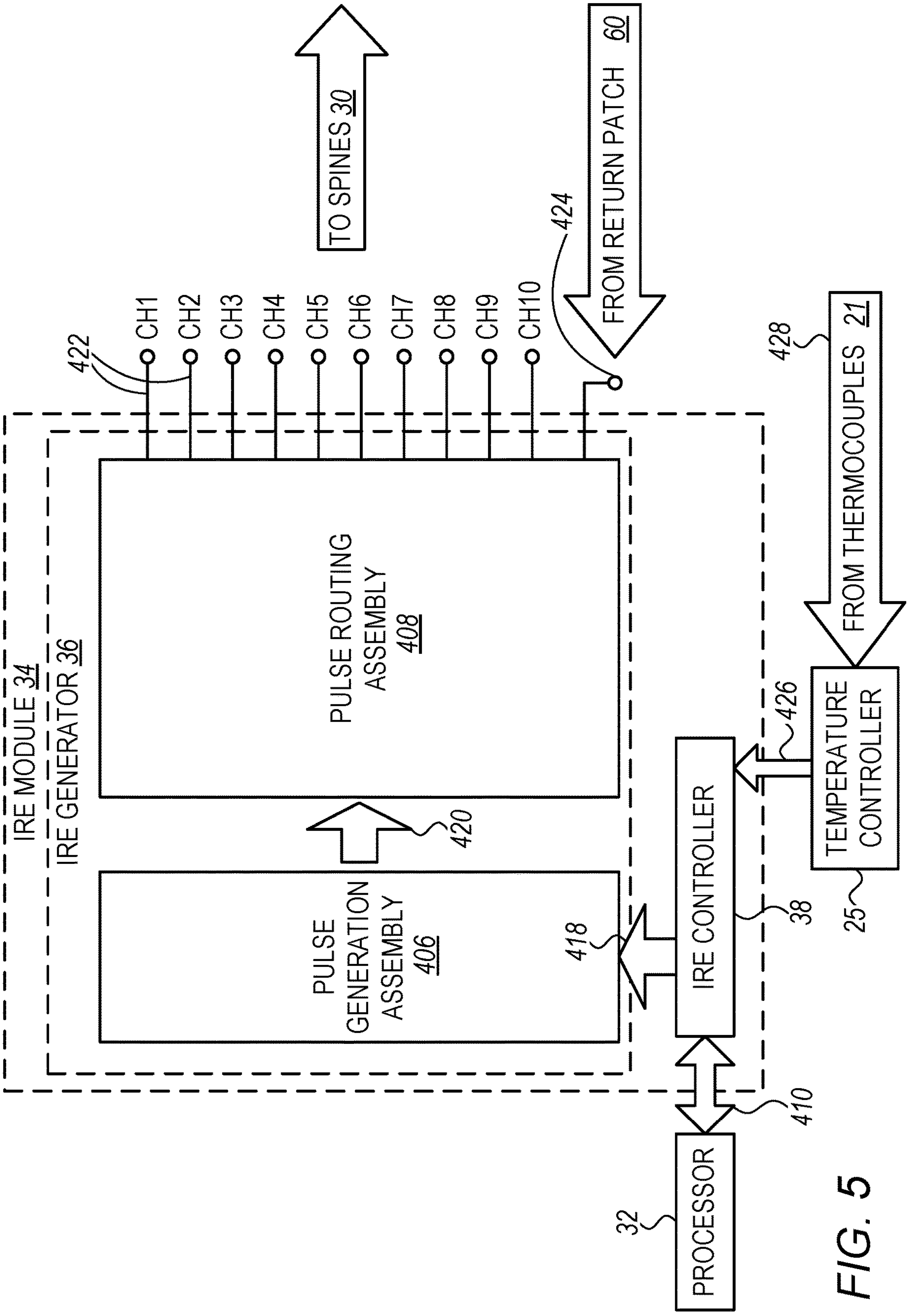
FIG. 5 is a block diagram that schematically illustrates an IRE module, in accordance with an exemplary embodiment of the invention.

FIG. 5 is a block diagram that schematically shows details of IRE module 34, in accordance with an exemplary embodiment of the present invention. As explained above in regard to FIG. 1, IRE module 34 comprises IRE generator 36 and IRE controller 38. IRE generator 36 comprises a pulse generation assembly 406 and a pulse routing assembly 408. Pulse generation assembly 406 is configured to receive control signals from IRE controller 38 (as described below) and to transmit sequences of bipolar pulses with an amplitude and duration responsive to the control signals. Pulse routing assembly 408 comprises a configurable network of switches, which are configured to receive control signals from IRE controller 38, to receive sequences of bipolar pulses from pulse generation assembly 406, and to select pairs of spines 30 responsively to the received control signals so as to the transmit the sequences of bipolar pulses through the selected pairs.

IRE controller 38 communicates with processor 32 through bi-directional signals 410, wherein the processor communicates to the IRE controller commands reflecting setup parameters 66. IRE controller 38 further communicates to pulse generation assembly 406 digital command signals 418, derived from setup parameters 66, commanding IRE generator 36 to generate IRE pulses, such as those shown in FIG. 4, above. These IRE pulses are sent to pulse routing assembly 408 as analog pulse signals 420, as directed by IRE controller 38.

IRE controller 38 receives command signals 426 from temperature controller 25, issued responsively to signals 428 output by thermocouples 21. Thus, temperature controller 25 controls the timing of the IRE pulses applied by IRE module 34 to spines 30 so that the temperature of tissue 62 adjacent to the spines does not exceed a preset limit.

Pulse routing assembly 408 is coupled to spines 30 through output channels 422, as well as (optionally) to return patch 60 through a connection 424. For example, when pulse routing assembly 408 is coupled to six spines 30*a*-30*f* of basket assembly 31 (FIG. 2), six of output channels 422 are coupled to the spines. Pulse routing assembly 408 is driven by IRE controller 38 to couple the IRE pulses into spines 30 as defined by setup parameters 66. Specifically, IRE controller 38 drives pulse routing assembly 408 to couple the IRE pulses to one or more selected pairs of spines 30. Routing assembly 408 may also electrically couple multiple spines 30 together to form a set that can serve as a "virtual electrode." Thus, IRE controller 38 controls both the generation and the routing of the IRE pulses into spines 30.

Although FIG. 5 shows ten channels 422, IRE generator may alternatively comprise a different number of channels, for example 8, 16, or 20 channels, or any other suitable number of channels.

Figure 6:
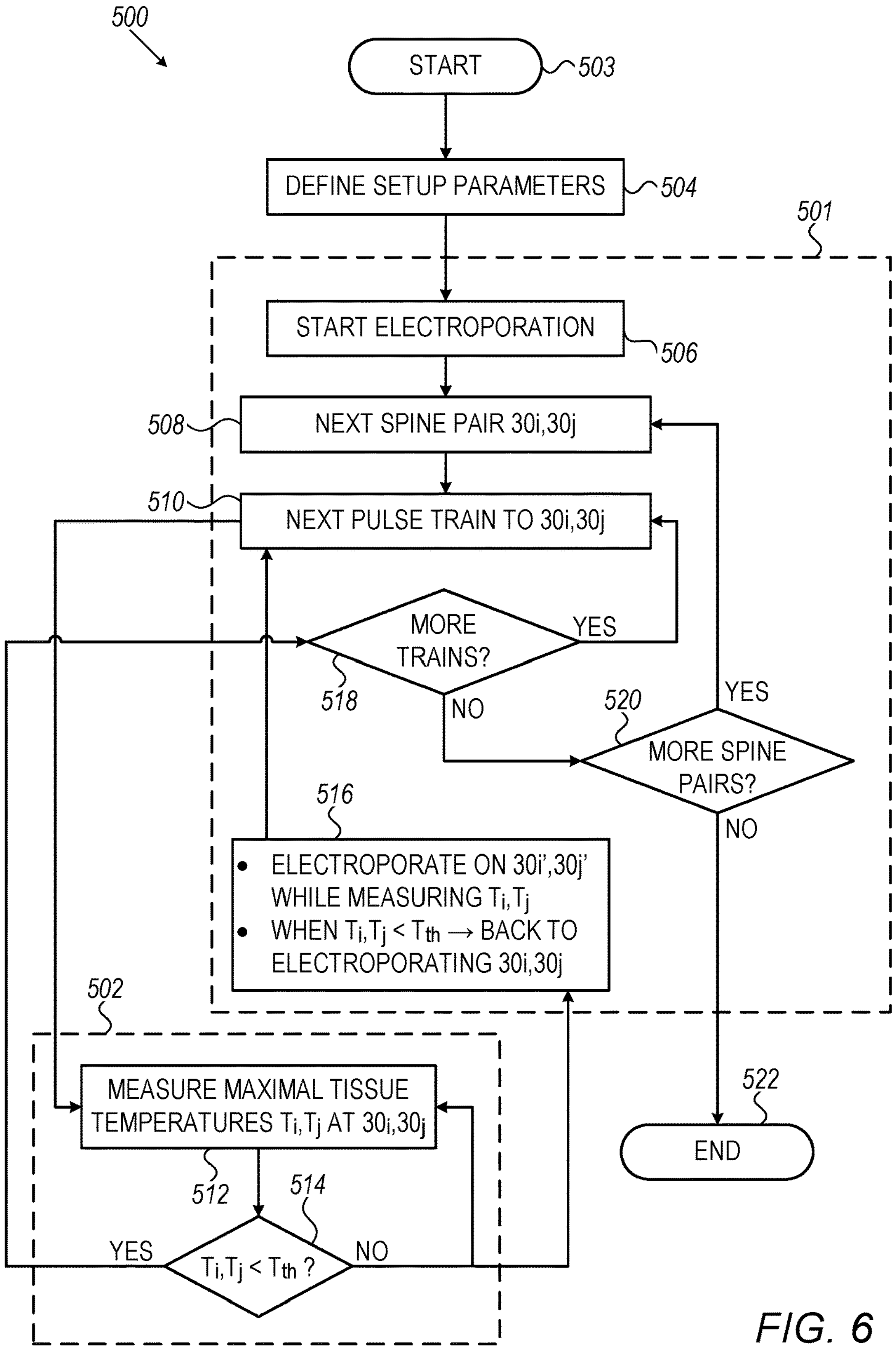
FIG. 6 is a flowchart that schematically illustrates a method for control of an IRE procedure using tissue temperature, in accordance with an exemplary embodiment of the invention.

FIG. 6 is a flowchart 500 that schematically illustrates the control of tissue temperature during an IRE procedure, in accordance with an exemplary embodiment of the invention.

In flowchart 500, the relevant functions of IRE module 34 and temperature controller 25 are shown by dotted-line frames 501 and 502, respectively. The IRE procedure starts at a start step 503. At a setup step 504, physician 22 (FIG. 1) defines setup parameters 66, including the preset limit $T_{th}$ for the temperature of tissue 62. IRE module 34 starts the generation of the IRE signals for the electroporation at an electroporation start step 506. IRE module 34 selects a spine pair 30*i*,30*j* in a next spine pair step 508, and generates and applies a new IRE pulse train to the spine pair, in a next pulse train step 510.

After and/or during the application of the pulse train, temperature controller 25 measures, using thermocouples 21, maximal temperatures $T_i$ and $T_j$ of tissue 62 adjacent spines 30*i* and 30*j*, respectively, in a temperature measurement step 512. In a temperature comparison step 514, temperature controller 25 compares the measured maximal temperatures $T_i$ and $T_j$ to the preset temperature limit $T_{th}$. As long as measured maximal temperatures $T_i$ and $T_j$ are below the preset limit $T_{th}$ (either directly after an IRE pulse or burst or after a suitable delay), temperature controller 25 indicates to IRE controller 38 that IRE module 34 may generate the next IRE pulse train.

If either of temperatures $T_i$ or $T_j$ is above $T_{th}$, temperature controller 25 continues measuring the temperatures of tissue 62. In the meanwhile, as indicated in an alternative pair step 516, electroporation is continued on an alternative pair of spines 30*i*',30*j*', with concomitant temperature measurements and precautions for not exceeding the preset limit $T_{th}$. Thus, temperature controller 25 gates the issuance of new IRE pulse trains to spines 30*i*,30*j* in response to the maximal temperatures of tissue 62 adjacent to these spines, specifically preventing new pulses from being issued if the tissue temperature exceeds the preset limit $T_{th}$. Once temperatures $T_i$ and $T_j$ have fallen to below $T_{th}$, temperature controller 25 signals this occurrence to IRE controller, which returns to generating pulse trains to spines 30*i*,30*j*, until the preset number of electroporation pulses have been issued through these spines. In case temperatures $T_i$ and $T_j$ again exceed $T_{th}$, the process reverts again to alternative pair step 516, possibly choosing another alternative pair of spines.

In a pulse train control step 518, IRE controller 38 checks against setup parameters 66 whether additional IRE pulses trains into spines 30*i*,30*j* are required. If the answer is affirmative, IRE module 34 generates another pulse train at step 510. When no more pulses are required into spines 30*i*,30*j*, IRE controller 38 checks in a spine control step 520 against setup parameters 66 whether electroporation signals need to be issued through additional pairs of spines. If the answer is affirmative, IRE module 34 chooses the next pair in next spine pair step 508. When no more spine pairs are left for electroporation, IRE controller 38 terminates the IRE procedure in an end step 522.

Figure 7:
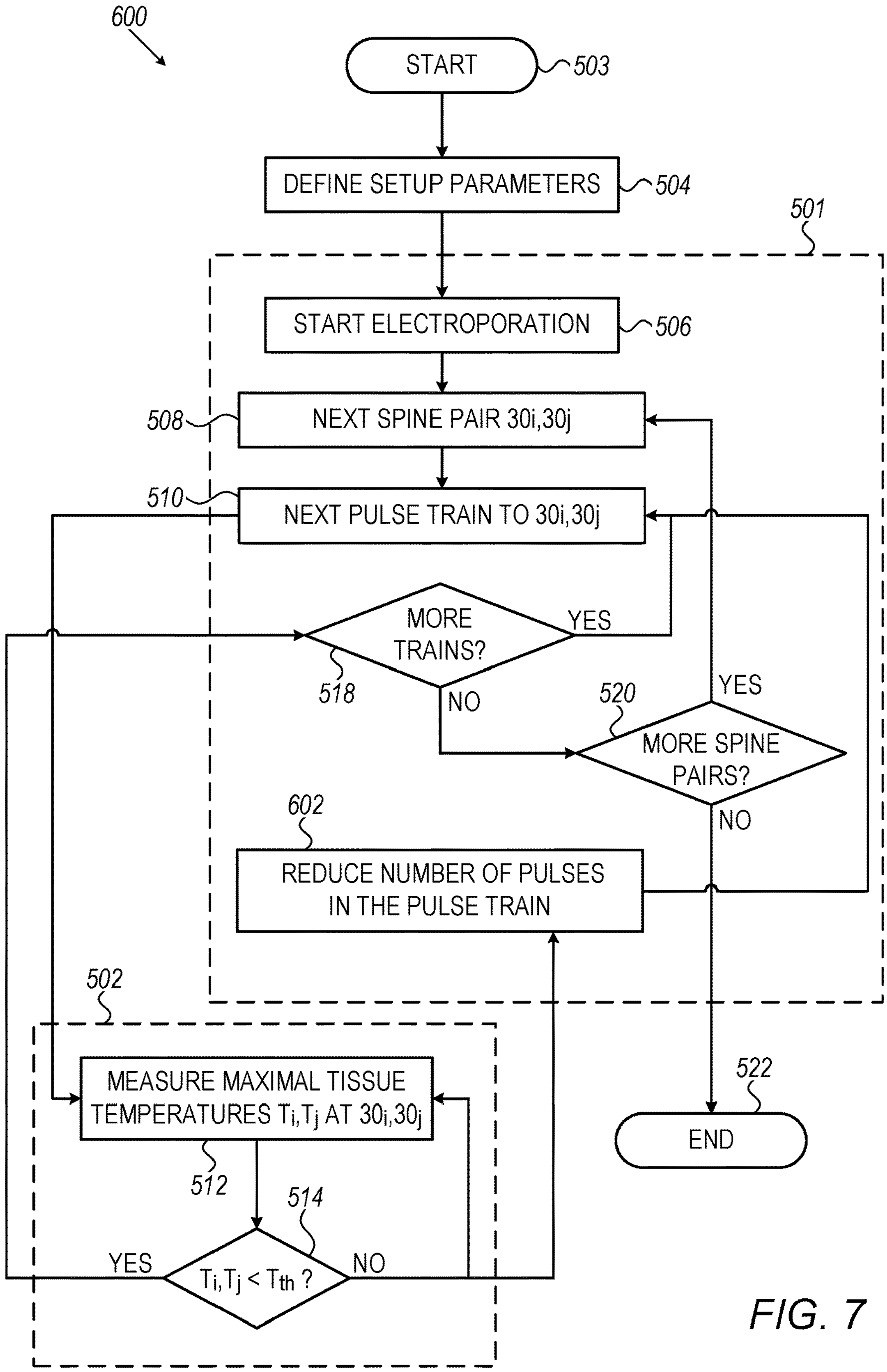
FIG. 7 is a flowchart that schematically illustrates a method for control of an IRE procedure using tissue temperature, in accordance with another exemplary embodiment of the invention.

FIG. 7 is a flowchart 600 that schematically illustrates a method for the control of tissue temperature during an IRE procedure, in accordance with another exemplary embodiment of the invention. Most of the steps in flowchart 600 are similar or identical to the steps in flowchart 500 (FIG. 6), and are labelled with the same numbers.

In the present exemplary embodiment, tissue temperature is controlled by reducing the number of pulses in a pulse train. Thus, if one or both of the temperatures $T_i$ and $T_j$ exceeds the preset limit $T_{th}$ at step 514, IRE controller 38 reduces the preset number of pulses in the pulse train to be applied to spine pair 30*i*,30*j*, in a pulse train reduction step 602. Once the temperatures $T_i$ and $T_j$ have fallen to below $T_{th}$ (or after a suitable delay), this reduced pulse train is applied to the spine pair. If necessary, the length of the pulse train is further reduced, until temperatures $T_i$ and $T_j$ stay below $T_{th}$. The number of pulse trains is increased in order to keep the total number of IRE pulses into a given spine pair at a preset value. Alternatively, the widths t+ and t− of the pulses and/or the pulse spacing $t_{SPACE}$ (FIG. 3) may be adjusted in order to lower temperatures $T_i$ and $T_j$.

In the described control processes, in order to avoid endless control loops, a maximum time can be set for the IRE process, and a maximum number is set for attempts for electroporation with a given spine pair. When the maximum time or number is reached, the process terminates.

The described control processes may also be applied, mutatis mutandis, to other types of catheters, with electrodes mounted on other sorts of distal structures, such as circular (lasso) catheters, balloon catheters, and linear catheters, as well as focal ablation catheters with a single tip electrode.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus for irreversible electroporation (IRE), comprising:

a probe, comprising:

an insertion tube configured for insertion into a body cavity of a patient, a distal structure connected distally to the insertion tube and comprising a plurality of electrodes, which are configured to contact tissue within the body, and temperature sensors fixed to the distal structure and configured to output signals indicative of a temperature of the tissue adjacent to the distal structure that is contacted by the plurality of the electrodes;

an electrical signal generator configured to apply a preset series of pulse trains to each of selected pairs of the plurality of the electrodes in turn, each pulse train of each of the preset series of pulse trains including a plurality of bipolar pulses having an amplitude sufficient to cause IRE in the tissue contacted by the selected pairs of the plurality of electrodes; and a controller programmed to:

cause a first preset series of pulse trains to be directed to a first pair of the plurality of electrodes while receiving signals from the temperature sensors indicative of a monitored temperature of the tissue adjacent to the distal structure that is contacted by the first pair of the plurality of the electrodes, cause, when the monitored temperature of the tissue contacted by the first pair of the plurality of electrodes rises above a preset threshold, the first preset series of pulse trains to be halted and a second preset series of pulse trains to be directed to a second pair of the plurality of electrodes, the second preset series of pulse trains being different than the first preset series of pulse trains, the second preset series of pulse trains continuing until the second preset series of pulse trains is complete or halted when a monitored temperature of the tissue contacted by the second pair of the plurality electrodes rises above the preset threshold, and cause, when the monitored temperature of the tissue contacted by the first pair of the plurality of electrodes falls back below the preset threshold and the second preset series of pulse trains to the second pair of the plurality of electrodes is one of: i) continuing, ii) completed, or iii) halted in response to the monitored temperature of the tissue contacted by the second pair of the plurality of electrodes rising above the preset threshold, the pulse trains of the first preset series of pulse trains that were not directed to the first pair of the plurality of the electrodes before the first preset series of pulse trains was halted, to be directed to the first pair of the plurality of the electrodes to complete the first preset series of pulse trains.

2. The apparatus according to claim 1, wherein the insertion tube comprises a flexible catheter configured for insertion into a chamber of a heart of the patient, and the plurality of electrodes are configured to contact and apply the electrical signals to myocardial tissue within the chamber.

3. The apparatus according to claim 1, wherein at least one of the first preset series of pulse trains or the second preset series of pulse trains applied by the electrical signal generator comprises a sequence of bipolar pulses having an amplitude of at least 200 V, and a duration of each of the bipolar pulses is less than 20 μs.

4. The apparatus according to claim 1, wherein the plurality of bipolar pulses comprises pairs of pulses, wherein each pair comprises a positive pulse and a negative pulse.

5. The apparatus of claim 1, wherein the controller is configured to repeat switching between directing the first preset series of pulse trains to the first pair of the plurality of the electrodes and the second preset series of pulse trains to the second pair of the plurality of the electrodes until the preset number of pulse trains have been applied to each of the first pair and the second pair of the plurality of electrodes.

6. The apparatus according to claim 1, wherein the controller is configured to:

modify the first preset series of pulse trains applied by the signal generator based on the temperature of the tissue contacted by the first pair of the plurality of the electrodes exceeding the preset threshold.

7. The apparatus according to claim 6, wherein modifying the first present series of pulse trains comprises preventing the electrical signal generator from applying the plurality of bipolar pulses on the first pair of the plurality of the electrodes.

8. The apparatus according to claim 6, wherein modifying the first preset series of pulse trains comprises modifying a number of successive bipolar pulses in the series applied by the signal generator to the first pair of the plurality of the electrodes.

9. The apparatus according to claim 6, wherein modifying the first preset series of pulse trains comprises delaying application of the plurality of bipolar pulses to the first pair of the plurality of the electrodes.

10. The apparatus according to claim 1, wherein the distal structure comprises a basket assembly comprising a plurality of resilient spines, which are configured to contact the tissue, wherein the temperature sensors are fixed to the spines.

11. The apparatus according to claim 10, wherein the spines have respective proximal and distal tips, wherein the proximal tips of the spines are joined mechanically at a proximal end of the basket assembly, and the distal tips of the spines are joined mechanically at a distal end of the basket assembly, and the spines bow radially outward when the basket assembly is deployed in the body cavity, thereby contacting the tissue in the body cavity.

12. The apparatus according to claim 10, wherein the spines comprise a conductive material and are configured to serve as the electrodes.

13. The apparatus according to claim 12, wherein the conductive material comprises a nickel-titanium alloy.

14. The apparatus according to claim 12, wherein each spine is divided into two or more mechanically connected but electrically isolated parts, wherein the electrically isolated parts of a given spine can be electrically connected together to serve as one of the plurality of electrodes for applying the plurality of bipolar pulses.

15. The apparatus according to claim 12, wherein the electrical signal generator is configured to apply the plurality of bipolar pulses between first and second sets of the spines, wherein at least one of the sets comprises two or more of the spines.

16. A method for medical treatment, comprising:

applying a preset series of pulse trains to each of selected pairs, respectively, of a plurality of electrodes on a distal structure of a probe in contact with tissue in a body cavity of a patient each pulse train of each of the preset series of pulse trains including a plurality of bipolar pulses having an amplitude sufficient to cause irreversible electroporation (IRE) in the tissue contacted by selected pairs of the plurality of electrodes;

causing a first preset series of pulse trains to be directed to a first pair of the plurality of electrodes while receiving signals from temperature sensors fixed to the distal structure indicative of a monitored temperature of the tissue adjacent to the distal structure that is contacted by the first pair of the plurality of the electrodes;

causing, when the monitored temperature of the tissue contacted by the first pair of the plurality of electrodes rises above a preset threshold, the first preset series of pulse trains to be halted and a second preset series of pulse trains to be directed to a second pair of electrodes, the second preset series of pulse trains being different than the first preset series of pulse trains, the second preset series of pulse trains continuing until the second preset series of pulse trains is complete or halted when a monitored temperature of the tissue contacted by the second pair of the plurality of electrodes rises above the preset threshold; and causing, when the monitored temperature of the tissue contacted by the first pair of the plurality of electrodes falls back below the preset threshold and the second preset series of pulse trains to the second pair of the plurality of electrodes is one of: i) continuing, ii) completed, or iii) halted in response to the monitored temperature of the tissue contacted by the second pair of electrodes rising above the preset threshold, the pulse trains of the first preset series of pulse trains that were not directed to the first pair of the plurality of the electrodes before the first preset series of pulse trains was halted, to be directed to the first pair of the plurality of the electrodes to complete the first preset series of pulse trains.

17. The method according to claim 16, wherein the insertion tube comprises a flexible catheter and wherein inserting the probe into a body cavity of a patient comprises inserting the catheter into a chamber of a heart of the patient, so that the plurality of electrodes contact myocardial tissue within the chamber and apply the electrical signals to the myocardial tissue.

18. The method according to claim 16, wherein applying at least one of the first preset series of pulse trains or the second preset series of pulse trains comprises applying a sequence of bipolar pulses having an amplitude of at least 200 V, and a duration of each of the bipolar pulses is less than 20 μs.

19. The method according to claim 16, wherein the plurality of bipolar pulses comprises pairs of pulses, wherein each pair comprises a positive pulse and a negative pulse.

20. The method of claim 16, further comprising repeating switching between applying the first preset series of pulse trains to the first pair and the second preset series of pulse trains to the second pair of the plurality of electrodes until the preset number of pulse trains have been applied to each of the first pair of the plurality of electrodes and the second pair of the plurality of electrodes.

21. The method according to claim 16, further comprising measuring temperature of the tissue contacted by the first pair of electrodes; and modifying the preset series of pulse trains applied while the temperature of the tissue contacted by the first pair exceeds the preset threshold.

22. The method according to claim 21, wherein modifying the preset series of pulse trains comprises preventing application of the plurality of bipolar pulses between the first pair of the plurality of electrodes.

23. The method according to claim 21, wherein modifying the preset series of pulse trains comprises modifying a number of successive bipolar pulses in the pulse trains applied to the first pair of the plurality of electrodes.

24. The method according to claim 21, wherein modifying the preset series of pulse trains comprises delaying application of the plurality of bipolar pulses to the first pair of the plurality of electrodes.

25. The method according to claim 16, wherein the distal structure comprises a basket assembly comprising a plurality of resilient spines contacting the tissue, and comprising temperature sensors fixed to the spines.

26. The method according to claim 25, wherein the spines have respective proximal and distal tips, wherein the proximal tips of the spines are joined mechanically at a proximal end of the basket assembly, and the distal tips of the spines are joined mechanically at a distal end of the basket assembly, and the spines bow radially outward when the basket assembly is deployed in the body cavity, thereby contacting the tissue in the body cavity.

27. The method according to claim 25, wherein the spines comprise a conductive material and are configured to serve as the electrodes.

28. The method according to claim 27, wherein the conductive material comprises a nickel-titanium alloy.

29. The method according to claim 27, wherein each spine is divided into two or more mechanically connected but electrically isolated parts, and applying the preset series of pulse trains comprises connecting the electrically isolated parts of a given spine together to serve as one of the electrodes for applying the bipolar pulses.

30. The method according to claim 27, wherein applying the preset series of pulse trains comprises applying the plurality of bipolar pulses between first and second sets of the spines, wherein at least one of the sets comprises two or more of the spines.

* * * * *